(12) United States Patent
Panat et al.

(10) Patent No.: US 12,188,892 B2
(45) Date of Patent: Jan. 7, 2025

(54) 3D PRINTED MICROELECTRODE ARRAYS

(71) Applicant: Carnegie Mellon University, Pittsburgh, PA (US)

(72) Inventors: Rahul Panat, Pittsburgh, PA (US); Eric A. Yttri, Pittsburgh, PA (US); Mohammad Sadeq Saleh, Pittsburgh, PA (US)

(73) Assignee: Carnegie Mellon University, Pittsburgh, PA (US)

( * ) Notice: Subject to any disclaimer, the term of this patent is extended or adjusted under 35 U.S.C. 154(b) by 1196 days.

(21) Appl. No.: 16/966,657

(22) PCT Filed: Jan. 31, 2019

(86) PCT No.: PCT/US2019/016050
§ 371 (c)(1),
(2) Date: Jul. 31, 2020

(87) PCT Pub. No.: WO2019/152648
PCT Pub. Date: Aug. 8, 2019

(65) Prior Publication Data
US 2021/0033559 A1  Feb. 4, 2021

Related U.S. Application Data

(60) Provisional application No. 62/766,572, filed on Oct. 26, 2018, provisional application No. 62/709,871, filed on Feb. 2, 2018.

(51) Int. Cl.
| | | |
|---|---|---|
| G01N 27/327 | (2006.01) |
| A61B 5/24 | (2021.01) |
| C09D 11/52 | (2014.01) |
| G01N 27/30 | (2006.01) |
| H05K 3/00 | (2006.01) |
| H05K 3/12 | (2006.01) |
| B33Y 10/00 | (2015.01) |
| B33Y 70/10 | (2020.01) |
| B33Y 80/00 | (2015.01) |

(52) U.S. Cl.
CPC ............. *G01N 27/327* (2013.01); *A61B 5/24* (2021.01); *C09D 11/52* (2013.01); *G01N 27/30* (2013.01); *H05K 3/0085* (2013.01); *H05K 3/125* (2013.01); *B33Y 10/00* (2014.12); *B33Y 70/10* (2020.01); *B33Y 80/00* (2014.12)

(58) Field of Classification Search
None
See application file for complete search history.

(56) References Cited

U.S. PATENT DOCUMENTS

| | | |
|---|---|---|
| 2003/0114936 A1 | 6/2003 | Sherwood et al. |
| 2007/0169333 A1 | 7/2007 | Donoghue et al. |
| 2013/0030274 A1 | 1/2013 | Jamieson et al. |
| (Continued) | | |

OTHER PUBLICATIONS

Saleh et al.,"Three-dimensional microarchitected materials and devices using nanoparticle assembly by pointwise spatial printing", Science Advances, 2017, vol. 3 pp. 1-8.

*Primary Examiner* — Hung K Vu
(74) *Attorney, Agent, or Firm* — The Webb Law Firm

(57) ABSTRACT

A high-density bioprobe array is provided comprising conductive or optical shanks. A method of making high-density bioprobe arrays also is provided. A bioprobe system using the array also is provided.

17 Claims, 9 Drawing Sheets

(56) References Cited

U.S. PATENT DOCUMENTS

2014/0350375 A1\* 11/2014 Wolfe ............. H01L 31/022408
                                                            438/42
2015/0351691 A1   12/2015 Lieber et al.
2016/0156045 A1   6/2016  Okuno et al.
2016/0167132 A1   6/2016  Panat \* cited by examiner

3D PRINTED MICROELECTRODE ARRAYS

CROSS REFERENCE TO RELATED APPLICATIONS

This application is the United States national phase of International Application No. PCT/US2019/016050 filed Jan. 31, 2019, and claims the benefit of U.S. Provisional Patent Application No. 62/709,871, filed Feb. 2, 2018, and U.S. Provisional Patent Application No. 62/766,572, filed Oct. 26, 2018, the disclosures of which are hereby incorporated by reference in their entirety.

Provided herein are high density microelectrode and optical arrays, systems comprising the arrays, and methods of making and using the arrays.

To understand and effectively treat neurological disorders, clinicians and researchers monitor the electrical activity of neurons across several brain areas. Diseases of the heart, skeletal muscles, and other tissue require comparable bioelectrical measurements. Highly delicate electrical probes are required to record such data. A platform to record and manipulate large numbers of neurons constituting neural circuits is desirable. To capture these neural dynamics, optimal recording must be done at the spatial and temporal resolution of neural interactions.

The electrical probes are also used to construct brain-machine interfaces that serves as the basis for the transformational field of neuroprosthetic devices. Such devices can restore movement to patients who are paralyzed or have undergone amputation allowing them to live with greater independence and an improved quality of life. Calcium imaging and functional imaging methods have provided good correlates of neural activity, albeit at slow timescales. While these techniques excel at covering larger areas of the brain, their spatial and temporal resolutions are currently insufficient to reconstruct the firing of action potentials. Additionally, calcium imaging is unable to measure signals from deeper brain structures without the insertion of large implants.

Microeletrode arrays (MEAs such as Utah array, Floating Microelectrode Arrays, NeuroNexus 'matrix' arrays) exist, utilizing various manufacturing methods such as microwire or lithography techniques on silicon boards. A significant issue facing these electrode arrays is the fragility of silicon, which becomes particularly apparent as the shank-count increases in larger probes and silicon MEAs. Further, if only few or more shanks break, it is not possible to selectively re-build them. Lastly, it is not straightforward to customize probe layouts that can provide great flexibility in designing experiments. This cost and lack of feasibility has resulted in barriers to entry that greatly limit scientific investigations, independent of their merit.

The recording density of current microelectrode technologies is rather limited. For example, high-density Utah array have probes that are in the range of 100-500 electrodes per square centimeter.

Robust and inexpensive bioelectrical probes which have increased recording areas and channel counts and are able to be integrated into adaptable, multi-functional platforms are therefore desirable.

SUMMARY

According to one aspect of the present invention, a method of preparing a high-density array of electrically-conductive, or optically-conductive shanks is provided. The method comprises depositing by aerosol jet printing, a plurality of shanks onto a surface of a substrate in a density of greater than 100 shanks per square centimeter ($cm^2$), greater than 500 shanks per $cm^2$, or greater than 1000 shanks per $cm^2$, of the surface of the substrate, each shank having a diameter ranging from 10 μm to 1 mm, and a length ranging from 10 μm to 10 cm, wherein the shanks are formed by depositing over the surface of the substrate a plurality of layers of a shank material solution comprising a conductive material dispersed in a liquid or a waveguide-forming material in a solvent, where each layer of the plurality of layers is deposited as an open shape having ends and a gap defined by the ends.

According to another aspect of the invention, a microprobe array is provided. The array comprises a plurality of conductive shanks and/or waveguide shanks over an LED on a surface of a substrate, each shank having a thickness ranging from 10μ to 1 mm, and ranging from 50μ to 1 cm in length, and disposed on the surface in a density of at least 100 shanks per square centimeter ($cm^2$), greater than 500 shanks per $cm^2$, or greater than 1000 shanks per $cm^2$, of the surface of the substrate. Uses to the microprobe array, e.g., in interfacing with tissue, such as nerve or neuronal tissue in a patient, also are provided.

According to another aspect of the invention, a bioprobe system is provided. The system comprises a microprobe or bioprobe array according to any aspect or embodiment provided herein, a plurality of leads attached independently to a plurality of conductive shanks of the array, and module configured to send to electrical signals to a shank or LED and/or receive an electrical stimulator from the shank, the module comprising a signal amplifier, a filter, and one or more processors and/or controllers configured or adapted to communicate electrical signals to and from the shanks or LEDs of the array.

According to another aspect of the invention, a method of interfacing with tissue in a patient, such as a neuron, is provided. The method comprises a microprobe or bioprobe array according to any aspect or embodiment provided herein in tissue, such as nerve or central nervous system tissue, of the patient so that a conductive surface of one or more conductive shanks of the array is positioned to administer an electrical signal to, or receive an electrical signal from tissue of the patient, and/or a waveguide shank is positioned to administer an optical signal to the tissue of the patient, and administering an electrical signal to the tissue of the patient, receiving an electrical signal from the tissue of the patient, and/or administering an optical signal to the tissue of the patient.

DETAILED DESCRIPTION

Figure 1:
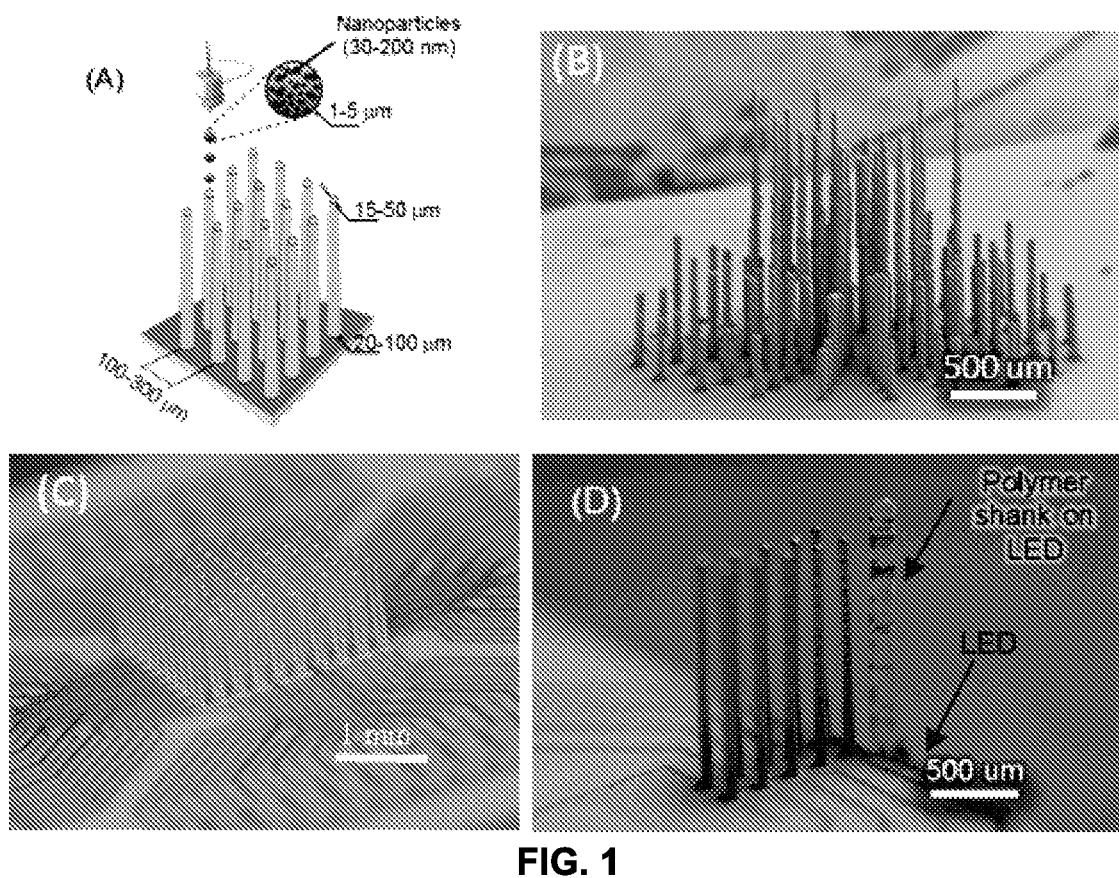
FIG. 1: 3D Printed Microelectrode Arrays (3DP-MEA). (A) Schematic of the Aerosol Jet 3D printing process. (B) Printed shanks of different lengths and diameters (length=100-650 um, diameters=35-50 um). Any combination of lengths is possible in finalized probe. (C) 100 shank probe that can easily be used in organisms as small as a mouse with printed PCB for connection. (D) 3D printed optic-fiber paired probe.

Other than in the operating examples, or where otherwise indicated, the use of numerical values in the various ranges specified in this application are stated as approximations as though the minimum and maximum values within the stated ranges are both preceded by the word "about". In this manner, slight variations above and below the stated ranges can be used to achieve substantially the same results as values within the ranges. Also, unless indicated otherwise, the disclosure of ranges is intended as a continuous range including every value between the minimum and maximum values. Further, as used herein, all numbers expressing dimensions, physical characteristics, processing parameters, quantities of ingredients, reaction conditions, and the like, used in the specification and claims are to be understood as being modified in all instances by the term "about". Moreover, unless otherwise specified, all ranges disclosed herein are to be understood to encompass the beginning and ending range values and any and all subranges subsumed therein. For example, a stated range of "1 to 10" should be considered to include any and all subranges between (and inclusive of) the minimum value of 1 and the maximum value of 10; that is, all subranges beginning with a minimum value of 1 or more and ending with a maximum value of 10 or less, e.g., 1 to 3.3, 4.7 to 7.5, 5.5 to 10, and the like.

As used herein "a" and "an" refer to one or more. The term "comprising" is open-ended and may be synonymous with "including", "containing", or "characterized by". The term "consisting essentially of" limits the scope of a claim to the specified materials or steps and those that do not materially affect the basic and novel characteristic(s) of the claimed invention.

As used herein, spatial or directional terms, such as "left", "right", "inner", "outer", "above", "below", and the like, relate to the invention as it is shown in the drawing figures. However, it is to be understood that the invention can assume various alternative orientations and, accordingly, such terms are not to be considered as limiting.

Further, as used herein, the terms "deposited over", "formed over", "over", or "provided over" mean formed, deposited, or provided on but not necessarily in contact with a surface. For example, a layer "formed over" a substrate does not preclude the presence of one or more other layers or films of the same or different composition located between the referenced structures. Likewise, the terms "under", or "provided under" mean formed, deposited, or provided beneath, but not necessarily in contact with a surface.

As used herein, the term "polymer composition" is a composition comprising one or more polymers. As a class, "polymers" includes, without limitation, homopolymers, heteropolymers, copolymers, block polymers, block copolymers and can be both natural and synthetic. Homopolymers contain one type of building block, or monomer, whereas copolymers contain more than one type of monomer.

A polymer "comprises" or is "derived from" a stated monomer if that monomer is incorporated into the polymer. Thus, the incorporated monomer that the polymer comprises is not the same as the monomer prior to incorporation into the polymer, in that at the very least, during incorporation of the monomer, certain groups, e.g. terminal groups, that are modified during polymerization are changed, removed, and/or relocated, and certain bonds may be added, removed, and/or modified. An incorporated monomer is referred to as a "residue" of that monomer. A polymer is said to comprise a specific type of linkage if that linkage is present in the polymer. Unless otherwise specified, molecular weight for polymer compositions refers to weight average molecular weight ($M_w$). A "moiety" is a portion of a molecule, compound or composition, and includes a residue or group of residues within a larger polymer.

As used herein, the unit "μm" refers to microns or micrometers, "cm" to centimeters, "nm" to nanometers, "Cp" to centipoise, and "cm$^2$" to square centimeters.

As used herein, the terms "polymer" or "polymeric" include oligomers, homopolymers, copolymers, and terpolymers, e.g., polymers formed from two or more types of monomers or polymers, and a "plastic" is a polymer-containing material that optionally can contain additional additives to alter a property of the material.

The terms "visible region" or "visible light" refer to electromagnetic radiation having a wavelength in the range of 380 nm to 800 nm. The terms "infrared region" or "infrared radiation" refer to electromagnetic radiation having a wavelength in the range of greater than 800 nm to 100,000 nm, and near infrared, referring to electromagnetic radiation having a wavelength in the range of 800 nm to 2,500 nm. The terms "ultraviolet region" or "ultraviolet radiation" mean electromagnetic energy having a wavelength in the range of 300 nm to less than 380 nm. By "transparent" is meant having visible light transmission of greater than 0% up to 100%.

A "waveguide" is a structure that guides waves, such as electromagnetic waves or sound, with minimal loss of energy by restricting expansion to one or two dimensions. In the context of the present invention a waveguide is formed as a shank, constraining travel of light in one dimension, to the tip of the waveguide, as in an optical fiber.

A "thermosetting polymer" or "thermoset" refers to a polymer composition that is hardened or cured by application of heat or suitable radiation. Non-limiting examples of useful photopolymers include: polyimides, acrylated urethanes, polyurethanes, epoxies, and epoxy based polymers such as SU8.

A "photopolymer" or light-activated resin is a polymer that changes its properties when exposed to light, often in the ultraviolet or visible region of the electromagnetic spectrum. Non-limiting examples of useful photopolymers include: SU8 polymer, acrylated epoxies, acrylated polyesters, acrylated urethanes, and acrylated silicones.

A "binder" or "binding agent" is any material or substance that holds or draws other materials together to form a cohesive whole mechanically, chemically, by adhesion or cohesion.

"Aerosol jet printing", also referred to as Maskless Mesoscale Materials Deposition or M3D, involves atomization of ink, e.g., by ultrasound or by pressurized gas, and entraining the ink droplets into a stream of gas for delivery to a print head that focuses the gas stream, for example using a gas sheath. Aerosol jet printing is capable of producing and accurately-depositing ink particles of 10 microns (p, or micrometers) or less. As such, aerosol jet printing is capable of producing structures/features 10μ or greater in size. Aerosol jet printing is capable of delivering suitably-sized nanoparticles, such as metals, carbon black, carbon allotropes (e.g., conductive carbon allotropes, such as graphite, carbon nanotubes, graphene, or fullerenes), and ceramics.

In order to prepare a high-density array of electrically-conductive or optically-conductive shanks (also referred to herein as "pillars"), a plurality of shanks of a conductive material or a waveguide-forming material are printed onto a surface of a substrate. FIG. 1 presents non-limiting examples of the high-density arrays or 'MicroElectrode Arrays' (MEA) described herein. The shanks may be cylindrical or tapered, e.g., conical or frusto-conical. The shanks are three dimensional, i.e. having a height of about a micron to several centimeters and having an aspect ratio between lateral dimension and length between 1:1-1:1000. The 'probe' or 'array' is the entire unit, consisting of 'pillars' or 'shanks' that are deposited on the surface of a substrate.

The shank material can be any conductive material, such as a metal, a conducting polymer, carbon black or a conductive carbon allotrope, and/or a doped semiconductor. In one non-limiting example, the shank material is metallic, and can comprise gold, silver, platinum, or copper, or alloys or mixtures of any of the preceding. In one aspect, the shank material is a metal, such as gold.

The shank material can be a waveguide-forming material, such as a transparent polymer. The waveguide-forming material can be a photopolymer or a thermosetting polymer. Non-limiting examples of waveguide-forming materials include, but are not limited to, acrylated urethanes, acrylates, methacrylates, such as poly(methyl methacrylate) (PMMA), photoresist polymers, polyimides, such as fluorinated polyimide, epoxies such as glycidyl ether of bisphenol A, such as SU-8 (from MicroChem), or siloxanes such as polydimethylsiloxane (PDMS) or a combination of such waveguide-forming materials, or any other polymers that can polymerize when dispensed from a nozzle and exposed to an energy source such as UV light or heat. Typical optical polymers useful for waveguides (waveguide-forming material) exhibit low optical loss (e.g., attenuation or transmission loss, such as <0.1 or 0.05 decibels per dB/cm) thermostable (>200° C., or >260° C.) polymer composition. However, due to the short length of the waveguides described herein, optical loss may be higher, such as up to 1 or 2 dB/cm, e.g., >1% or >10% transmittance through the formed waveguide shank.

Each shank of the probe is of the same or different materials. If the printed shanks are of different materials, the material is either mixed prior to printing or printed sequentially.

The shank material is dispersed in a liquid medium to form a shank material solution. Non-limiting examples of suitable liquids for the liquid medium include deionized water, ethylene glycol, toluene, hexane, 2-methoxyethanol, glycerol, 2-amino-2-methyl-1-propanol (AMP), tetradecane, or a combination of two or more liquids. The shank material solution may additionally comprise a rheology modifier, such as ethylene glycol, N-vinylpyrrolidone, or hydrophobically modified ethylene oxide urethane (HEUR), or a combination of two or more rheology modifiers. Conductive shank material may comprise nanoparticles, such as metal nanoparticles. The metal nanoparticles may be coated with a polymer in order to avoid agglomeration in the dispersion. The shank material solution may comprise a binder or binding agent. Useful binding agents for metal nanoparticles, such as in the context of conductive ink include, without limitation: polyalkylene carbonates, acrylic resins, or 2-methoxyethanol, or a combination of two or more of binding agents.

Figure 2:
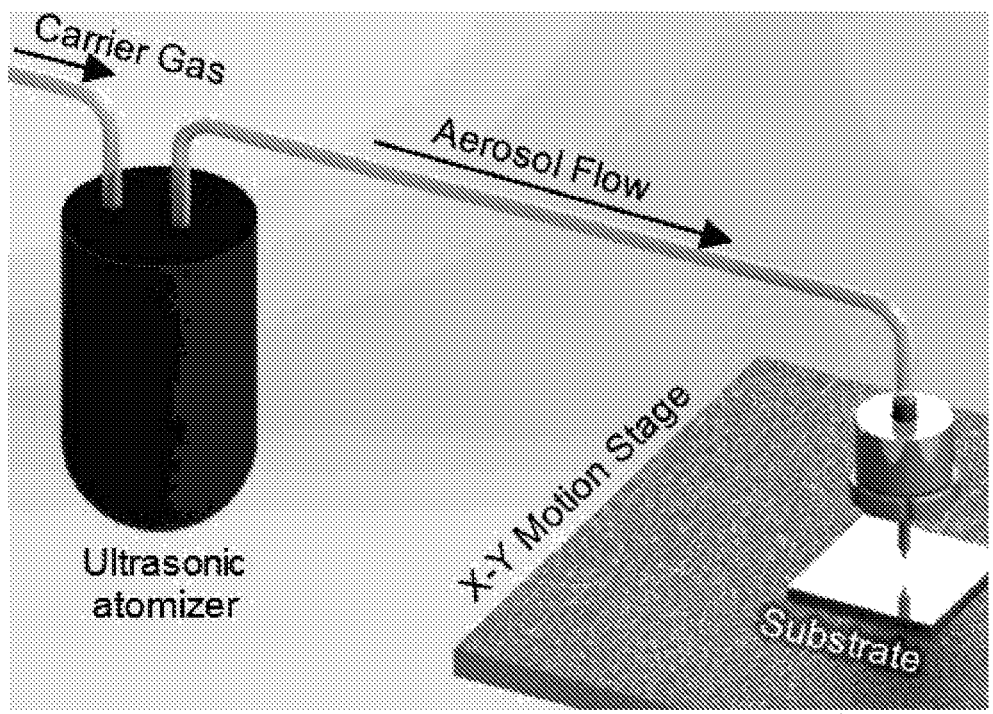
FIG. 2: Schematic of aerosol Jet printing process for fabrication of 3DP-MEA probes.

The shanks are deposited onto the surface of the substrate by printing methods such as aerosol jet (AJ) printing, as shown in FIG. 2, or inkjet printing. The AJ printer creates an aerosol mist of the droplets of the shank material solution using either a pneumatic or an ultrasonic atomizer and utilizes an aerodynamic focus to deposit aerosolized materials such as metal nanoparticles onto the substrate. Pneumatic atomization is used for the printing of thicker liquids such as polymers. The aerosol jet printing can be carried out with an atomizer gas flow rate of 1-30 sccm (standard cubic centimeters per minute) and a sheath gas flow rate of 1-70 sccm, which varies with particular liquid media and viscosities.

Figure 3:
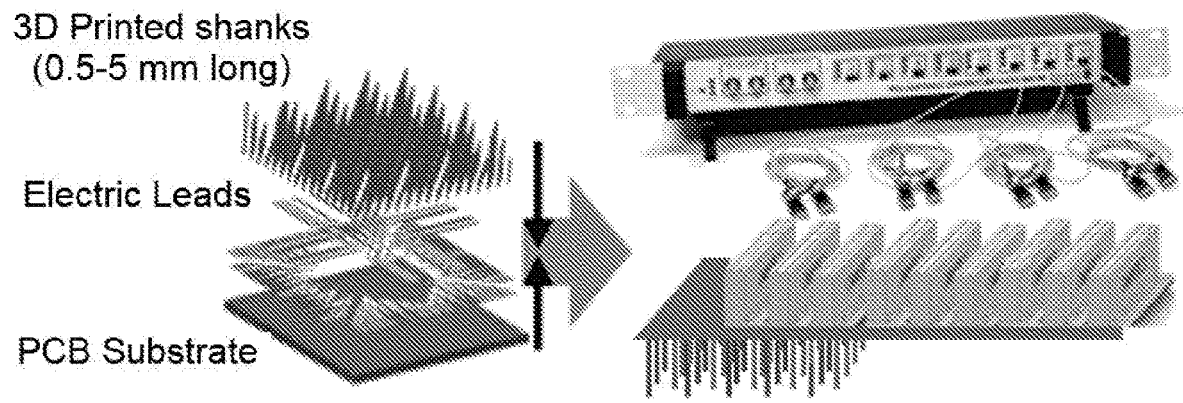
FIG. 3: Schematic of 3DP-MEA probe production: Nanoparticle printed, insulated shanks are constructed onto electric leads of a custom-made printed circuit board (PCB). In examples, the 3DP-MEA custom circuit board is outfitted with several Omenitcs connectors that route voltages out to an Intan 1024 channel recording controller.

Non-limiting examples of suitable substrates include flexible or rigid polymer, metal, alumina, ceramic, diodes, integrated circuit, or circuit board such as a printed circuit board (PCB), as shown in FIG. 3. Examples of flexible polymers include but are not limited to polydimethylsiloxane (PDMS), Kapton, or Poly(lactic acid) (PLA). The shanks and/or pillars are printed on a substrate that is flat or curved. The shanks and/or pillars can be printed directly on pads of a PCB that is pre-wired for connection to a recording device.

Figure 4:
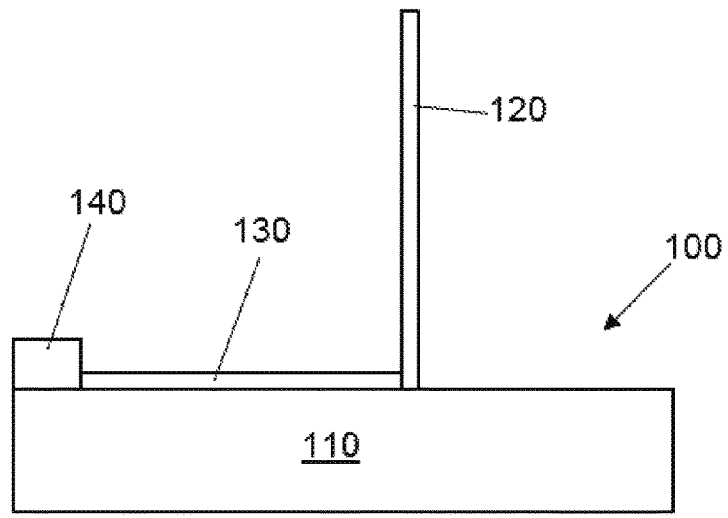
FIG. 4 depicts schematically (not to scale) a cross section of a conductive probe structure according to one embodiment of the invention.

Each conductive shank has at least one 'electrode' or 'recording site', which sends bioelectric signals along conducive traces (or leads, pads, etc.) to electrical connectors to electrically connect additional electronic components to the shank. The electrical signals are then sent to a data acquisition system. As shown in FIG. 4, a probe structure 100 is depicted schematically, comprising a substrate 110, such as a printed circuit board substrate (PCB) comprising a three dimensional shank 120, a conductive trace 130 is electrically-connected to the shank 120, and an electrical connector 140 is electrically connected to the conductive trace 130. Although shown in FIG. 4 as being over the substrate 110, the trace 130 and connector 140 may be integrated into or arranged relative to the substrate 110 in any suitable manner. Trace 130 may be contiguous with the shank, in that it is deposited by aerosol jet printing at the same time the shank 120 is deposited. Likewise, connector 140 may be contiguous with the trace 130, and may be co-deposited with the trace 130 and/or the shank 120. FIG. 4 depicts a single shank 120 for clarity, but it is understood that a probe structure as described herein can include a plurality of shanks and traces, for example and without limitation, ranging from two to 10,000 or more shanks, traces, and connectors, arranged in any suitable pattern on the substrate. One or more shanks may be attached to each trace and connector or one or more shanks and traces may be attached to each connector. In one embodiment, each shank has a single trace and a single connector, and as such, each shank is individually addressable. In another embodiment, a plurality of shanks are connected to a single trace and a single connector, and/or a plurality of shanks and traces attached to single shanks are connected to a single connector, such that shanks are not individually addressable, provided there are at least two leads and connectors, groups of shanks, for example, two to 100 shanks in an array of shanks may be individually addressable. It is understood in this, and in other embodiments described herein, that the 2D and 3D topological arrangement of the shanks, conductive traces, leads, or wires, and connectors, and the nature and composition thereof can vary greatly as a matter of design optimization. Likewise, the manufacturing method and compositions of the substrate, traces, leads, or wires, and connectors, may vary greatly, so long as they are suitable for the intended purpose.

Figure 5:
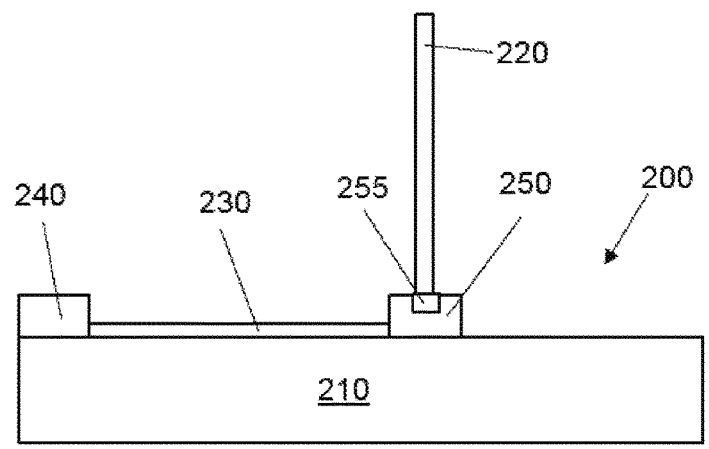
FIG. 5 depicts schematically (not to scale) a cross section of an optical probe structure according to one embodiment of the invention.

In another embodiment, depicted in FIG. 5, a probe structure 200 comprises an optical pillar. The probe structure 200 comprises a waveguide pillar 220, an electrical trace 230, an electrical connector 240, and a light-emitting diode (LED) 250 comprising an emitter 255 that directs light to the waveguide 220. Trace 230 and connector 240 are essentially as described in FIG. 4, though they are used to deliver power to the LED 250. The LED 250 emits electromagnetic radiation in any wavelength or spectrum, and may comprise more than one emitters, and any additional components, such as a lens, a filter, or light shielding structure to prevent stray light emissions. One or more LEDs and waveguide pillars may be attached to each trace and connector or one or more LEDs, waveguide pillars and traces may be attached to each connector. In one embodiment, each LED and waveguide pillar has a single trace and a single connector, and as such, each LED and waveguide pillar is individually addressable. In another embodiment a plurality of LEDs and waveguide pillars are connected to a single trace and a single connector, and/or a plurality of LEDs, waveguide pillars, and traces attached to single shanks are connected to a single connector, such that LEDs and waveguide pillars are not individually addressable, provided there are at least two leads and connectors, groups of LEDs and waveguide pillars, for example, two to 100 LEDs and waveguide pillars in an array of LEDs and waveguide pillars may be individually addressable. It is understood in this, and in other embodiments described herein, that the 2D and 3D topological arrangement of the LEDs, waveguide pillars, conductive traces, leads, or wires, and connectors, and the nature and composition thereof can vary greatly as a matter of design optimization. Likewise, the manufacturing method and compositions of the substrate, traces, leads, or wires, and connectors, may vary greatly, so long as they are suitable for the intended purpose.

Further, one or more LEDs and waveguide pillars, e.g., as depicted schematically in FIG. 5, are arranged on the same substrate as one or more shanks, e.g., as depicted schematically in FIG. 4. In such an embodiment, the one or more LEDs may be used to emit light, to stimulate a physiological reaction in a tissue, and the one or more shanks are used to receive electrical signals and transmit the signals to a controller such as a recording controller for receiving, amplifying, analyzing, converting, and/or storing the signals and data or representations of the data produced from the signals, and providing an output, such as visual, digital, or printed output, representing the data obtained from the shanks. The data obtained from the shanks, and data representing the data obtained from the shanks can be received, transmitted or communication, amplified, analyzed, processed, converted, represented, stored, and output in any suitable manner and using any suitable software and hardware, e.g., as are known in the computing and software arts.

Figure 6:
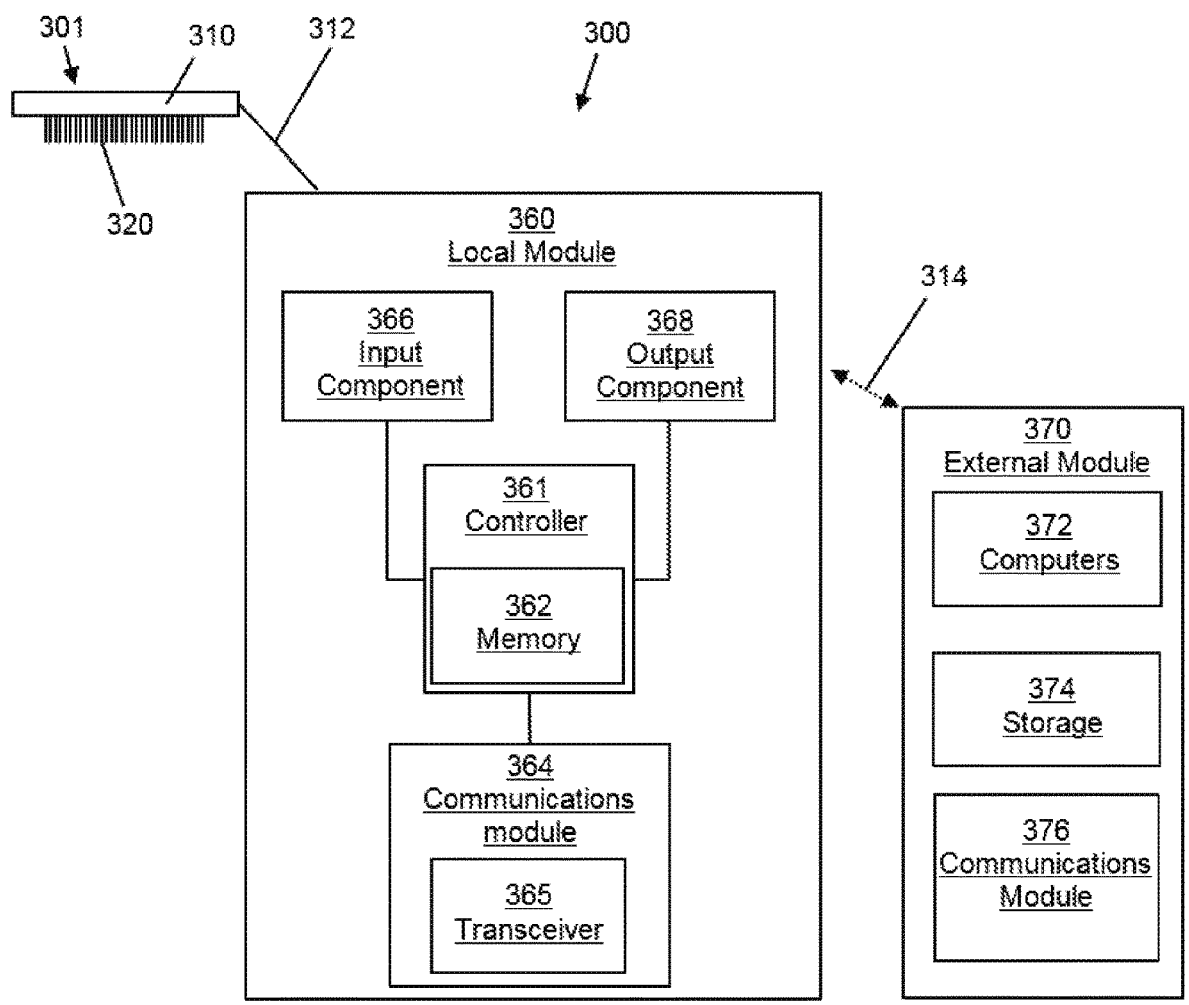
FIG. 6 depicts schematically a system according to one embodiment of the invention.

FIG. 6 depicts schematically one embodiment of a system as described herein. System 300 comprises a probe array 301 comprising a substrate 310 and a plurality of shanks and/or waveguide pillars 320. The substrate comprises the electrical traces, electrical connectors, and/or LEDs, for example as described in connection with FIGS. 4 and 5, which are not shown for clarity. The probe array 301 may comprise only waveguide pillars and LEDs, or only conductive shanks, or both, depending on the desired use. The probe array 301 is electrically-connected 312 to a local module 360. The local module 360 comprises any required elements for powering the system 300, such as batteries, e.g., rechargeable batteries and/or a power supply, such as a DC power supply for powering other local components of the system, signal amplifier(s), analog-to-digital (ND) converters, or communication modules for communicating with other parts of the system, either wirelessly, or wired. The local module 360, as depicted, comprises a controller 361, memory 362, a communications module 364, an input component 366, and an output component 368. It is understood that the local module 360 may be a separate, wired structure, or integrated into the substrate 310, e.g., circuit board. In aspects, the local module 360 may comprise a BIOS, one or more signal amplifiers, one or more analog-to-digital converters, memory, storage, processor(s), additional electronic hardware components, and/or computer-readable instructions for controlling the local module and/or for communication within the system or with a separate device, e.g., as are known in the computing arts. Also included in the system 300 is an external module 370, comprising a communication module for communicating 314 wirelessly or by a wired connection to the local module 360. The external module 370 is shown comprising one or more computers 372, storage 374, and a communications module for communicating with other elements of the system 300 and, optionally, additional computers and/or computer networks. The external module 370 also may comprise a BIOS, one or more signal amplifiers, one or more analog-to-digital (ND) converters, memory, storage, processor(s), additional electronic hardware components, and/or computer-readable instructions for controlling the local module and/or for communication within the system or with a separate device, e.g., as are known in the computing arts. In one aspect, the external module 370 comprises a computer, such as a personal computer, a laptop, a smartphone, or a dedicated controller device, such as, for example and without limitation, an Intan RHD2000-64 ch digital head stages and 1024 ch recording controller. The external module 370 may communicate with the local module 360 via a wireless connection, such as by near-field communication (NFC), Zigbee, or Bluetooth protocols. External module may be connected to any suitable output device, including displays, printers, or may communicate with one or more additional external devices, such as computers or computer networks via any suitable communication means, such as a computer network or over the Internet. System 300 is merely exemplary, and data may be obtained from the conductive shanks, and power may be provided to the LED(s) and/or conductive shanks by any suitable arrangement of local modules 360 and external modules 370, and elements thereof, such as power supplies, signal amplifiers, analog-to-digital (ND) converters, memory, storage, processor(s), communication devices, additional electronic hardware components, and/or computer-readable instructions for controlling any aspect of the system, e.g., as are known in the computing arts.

Further, referring to FIG. 6, in some examples, the local module 360 comprises a controller 361 for executing functions related to receipt, analysis, and transmission of sensed movement data. In some examples, a controller is a central processing engine including a baseline processor, memory, and communications capabilities. For example, the controller 361 can be any suitable processor comprising computer readable memory 362 and configured to execute instructions either stored on the memory 362 or received from other sources. Computer-readable memory 362 can be, for example, a disk drive, a solid-state drive, an optical drive, a tape drive, flash memory (e.g., a non-volatile computer storage chip), cartridge drive, and control elements for loading new software.

In some examples, the controller 361 includes a program, code, a set of instructions, or some combination thereof, executable by the local module 360 for independently or collectively instructing the local module 360 to interact and operate as programmed, referred to herein as "programming instructions". In some examples, the controller 361 is configured to issue instructions to one or more of the probes 301 to initiate data collection and to select types of measurement information that should be recorded. In other instances, the probe(s) 301 is configured to automatically transmit all sensed movement data to the intermediary local module 360 either in real time or at periodic intervals without first receiving initiation instructions from the controller 361 to initiate sensing and data transmission.

In either case, as will be discussed herein, the controller 361 is configured to receive and process movement information from the probe(s) 301 for activities performed by the subject. Processing can include applying filters and other techniques for removing signal artifacts, noise, baseline waveforms, or other items from captured signals to improve readability. As discussed in greater detail in connection with the discussion of FIGS. 4 and 5, processing information includes data analysis techniques, such as quantifying various movement parameters based on received data, corroborating or calibrating data from multiple sources, and/or analyzing generated movement parameters to draw conclusions about the subject.

In one example for analyzing received data, the controller 361 is configured to compare one or more inertial data sets obtained from the probe(s) 301 with reference data comprising one or more reference inertial data sets stored on the computer readable memory or received from external sources, such as the external module 370. For example, the reference inertial data sets can be stored on the storage 374 and transmitted to the intermediary local module 360 via the external module 370. In some examples, the reference inertial data sets include average parameter values or target parameter values for individuals having similar physical characteristics to the subject. The controller 361 can be configured to determine one or more deviations, if any, between the inertial data set(s) and the reference inertial data set(s), and, if one or more deviations is present, generate a list of one or more activities or actions (e.g., a recommended treatment regimen) that the subject could perform as a corrective measures to address the identified deviations between the subject's inertial data set and the average or target data set for similarly situated individuals. Possible corrective actions, in the form of a treatment regimen or treatment protocol, can also be stored on a database on the storage 374 and transmitted to the intermediary local module 360 by the external module 370 when required.

In some examples, the intermediary local module 360 comprises a communications module 364 associated with the controller 361. In that case, the controller 361 is configured to cause the communications module 364 to transmit the raw, processed, or analyzed data from the wearable sensor device(s) to remote sources, such as the external module 370. In other examples, the data is uploaded from the intermediary local module 360 to an internet webpage or other remotely accessible database.

The communications module 364 comprises a data transceiver 365 for short-range, medium-range, or long-range communication with the communications module 376. For example, the short range data transceiver may be a Bluetooth® transceiver, Zigbee transceiver, a cellular transceiver, a radio frequency (RF) device, or any other wireless data transmission device, as are known in the art. In other examples, the communications module 364 comprises a wired data transmission interface. In that case, the external module 370 can be connected to the local module 360 using a USB cable or similar data transmission cable. The communications module 364 can also include a long-range wireless data transceiver 365 for communication with the computer(s) 372 of the external module 370. For example, long range data transmission can use WiFi, cellular, radio frequency, satellite, and other known data transfer devices and protocols. Communication between the communications modules 364, 376 can be encrypted by any useful method. In that case, the communications module 376 can be configured to receive encrypted data from the local module 360 and process the encrypted data to remove encryption so that the received device can be analyzed. For example, the modules 360, 370 can use encryption, data redaction, and/or security mechanisms to ensure data privacy and that the system comports with privacy standards, such as the U.S. Health Insurance Portability and Accountability Act (HIPAA) standards.

In some examples, the intermediary local module 360 further comprises an input component 366 and an output component 368 in communication with the controller 361, which allow the user to interact with and receive feedback from the local module 360. The input component 366 includes one or more of a keyword, touchpad, computer mouse, trackball, or other data entry accessory, as are known in the art. In other examples, input components 366 include a microphone for capturing audio data entry by a user or optical or motion sensors for capturing gestures performed by the user. The input component 366 can be used to enter information about the subject which can be used to analyze the measurement data and/or to assist in gait analysis and training regimens. For example, information about the subject's gender, age, height, weight, activity level (e.g., recreationally active, occupationally active, soldier, elite athlete), and other relevant information can be entered via the input component 366. The input components 366 can also be used to interact with a user interface by, for example, being able to toggle through instruction screens for configuring the electrical signals provided to or received from each shank or pillar 320 of the probe 301. User interface screens that can be shown on a visual display and used for entering information and guiding a user in collecting information about a subject.

In some examples, the input/output components 366, 368 is a touch screen display. In other examples, output component 368 includes a visual display, speakers, haptic output devices, and/or other types of feedback devices as are known in the art. The output component 368 can provide feedback to a clinician about the subject's physical condition and, in particular, feedback based on movement information captured by the probe 301.

In addition to providing feedback, in some examples, the controller 361 is configured to cause the output component 368 to provide visual or audio instructions to the user or subject related to the movement assessment being performed, such reminders that assist the patient to remember what to focus on when walking. More than one output component 368 may be utilized, such as a screen for a clinician in addition to the display device.

The components of the probe 301, local module 360, and external modules 370 can be combined in various manners with various analog and digital circuitry, including controllers, filters, ADCs (analog-digital chips), memory, communication devices and/or adaptors. As devices become smaller and processors become more powerful and use less energy, it is possible to integrate many more electrical and electronic components into the local module. Technologies such as package on package (PoP) and system on a chip (SoC) integrated circuit packages allow manufacture of very small devices with significant capacities. For example, smart phones use PoP technologies to stack memory and processors in a very small volume. One example of a SoC is a microcontroller (MCU), which is a small computer on a single integrated circuit typically containing a processor core, memory, and programmable input/output peripherals. MCUs also may include timer module(s) and analog-to-digital converter(s) for, e.g., converting analog sensor output to a digital signal.

With continued reference to FIG. 6, in some examples, the local module 360 is in communication with the storage 374 of the external module 370. For example, the local module 360 can receive information including patient information and reference data sets from databases stored on the storage 374. For example, the storage 374 can comprise a stimulation protocol for a subject and/or a protocol for receiving and analyzing data received from a subject. A health record contains personal information for the subject such as a subject's name, age, weight, height, body mass index (BMI), and blood pressure also can be stored in storage 374. A health record can also contain information about assessments previously performed by the subject or about a subject's history. The local module 360 can, for example and without limitation, store, communicate the personal information, and combine the personal information with the probe data set information for communication to other external computer devices, such as the computer 372. In some examples, the local module 360 is also configured to redact private information from the personal information prior to communication of the personal information. The received patient information is used by the computer 372 to improve analysis of the sensed movement information.

The storage 374 may comprise a database of reference data sets with stimulation or received information for a wide range of subjects, or parameters based on other sources, such as from research studies. The database can be used to obtain reference datasets for other individuals with similar characteristics as the subject. Measurements for the subject can be compared with reference data sets for improve specificity and accuracy in tissue stimulation or data analysis. In some instances, reference data sets are based on statistical (e.g., average) values for segments of a population (e.g., segments of the overall population with physical characteristics similar to the subject) or for the population generally. In other examples, a set of reference data sets is provided from the database for individuals with varying conditions, e.g., diseases and disease states. In one example, the database includes a reference data set or individual classified sets for a normal or control individual with no relevant condition, as well as for individuals with the relevant condition. The measured data set for the patient can be compared to data sets for others, or other reference values. As information for different subjects is obtained, processed, and analyzed, the database can be expanded in an iterative manner to improve specificity and accuracy for any condition.

Referring to FIGS. 4-6, in use, the shanks 120, 220, 320 of the probe array 100, 200, 301 may be implanted in a tissue. Depending on the use and design of the probe array, any conductive shank can be used to produce an electrical stimulus or to receive an electrical signal from the tissue, or both in any sequence. The waveguide shanks can produce light to serve as a stimulus, such as an optogenetic stimulus. A probe array as described herein, comprising conductive shanks and waveguide shanks can be used to controllably photostimulate neural populations and record them simultaneously. Because the shanks can be individually addressable, or addressable in groups of two or more, different electric signals can be sent to each addressable shank or groups of shanks, and different addressable shanks or groups of shanks can serve to receive electrical signals from the tissue. One use for the probe arrays and system described herein is for stimulating and/or receiving signals from neurons or brain cells. The array can be inserted into nerve or neuronal tissue, e.g., CNS, such as brain or spinal cord tissue and conductive shanks can receive signals from the nerves to map or otherwise follow activity of the nerve or neuron. one or more of the shanks can be used to provide an electrical signal, such as a pulse, series of pulses, or a continuous current to a tissue, such as a nerve or neuronal cell, and subsequently, after discontinuance of the applied electrical signal, a signal can be received to determine the effect of such stimulus. In one example, for optogenetic approaches, light of a suitable wavelength and intensity can be directed to a tissue location by the waveguide shanks, e.g., as shown in FIG. 5, to stimulate cells, and optionally conductive shanks in the same array or a different array are used to monitor signals and therefore a response in the tissue. As with the conductive shanks, a plurality of waveguide shanks over independently-addressable LEDs may be provided, such that one, more than one, or all such waveguide shanks produce a light signal, thereby tailoring the extent of the stimulation of modified cells.

In further detail, and with respect to various elements and components described herein, when the substrate is an integrated circuit or a circuit board, the shanks are electrically-connected to interconnects of the integrated circuit or traces of a circuit board. Interconnects, traces, wires, or other conductive structures connected to the shanks to provide an electric signal to and/or receive an electric signal from, the shanks are referred to collectively as "leads". Leads may also be electrically connected to or terminated by one or more electrical connectors, such as plugs, adaptors, terminals, clips, binding posts, pinouts, headers, mating connectors, ports, crimp connectors, etc., as are broadly known in the electrical and electronic arts for electrically connecting conductors, such as leads.

The electrical connectors can be printed or made by conventional method. The traces or electrical connectors on the PCB may be deposited by aerosol jet printing. The electrical connectors are made of conductive material, such as metal, and are in a single or multiple stacked planes with polymer, e.g., polyimide insulation in-between. The electrical connectors are made using conventional methods such as lithography or made by printing and sintering of metal particles and printing and curing of polymer insulation.

A plurality of leads may be attached independently to a plurality of conductive shanks of the array. The shanks may be independently addressable, meaning they are connected to different circuits, leads, traces or interconnects and as such, can conduct different signals for either stimulation, or for receiving electrical signals. Likewise, pillars can be independently addressable, meaning they are deposited over LEDs that are connected to different circuits and can be activated individually and independently. The conductive shanks may be connected to an electrical stimulator or a receiver, such as an electroencephalogram receiver optionally comprising a signal amplifier, a filter, and one or more processors and/or controllers configured or adapted to receive electrical signals from the shanks of the array.

Figure 7:
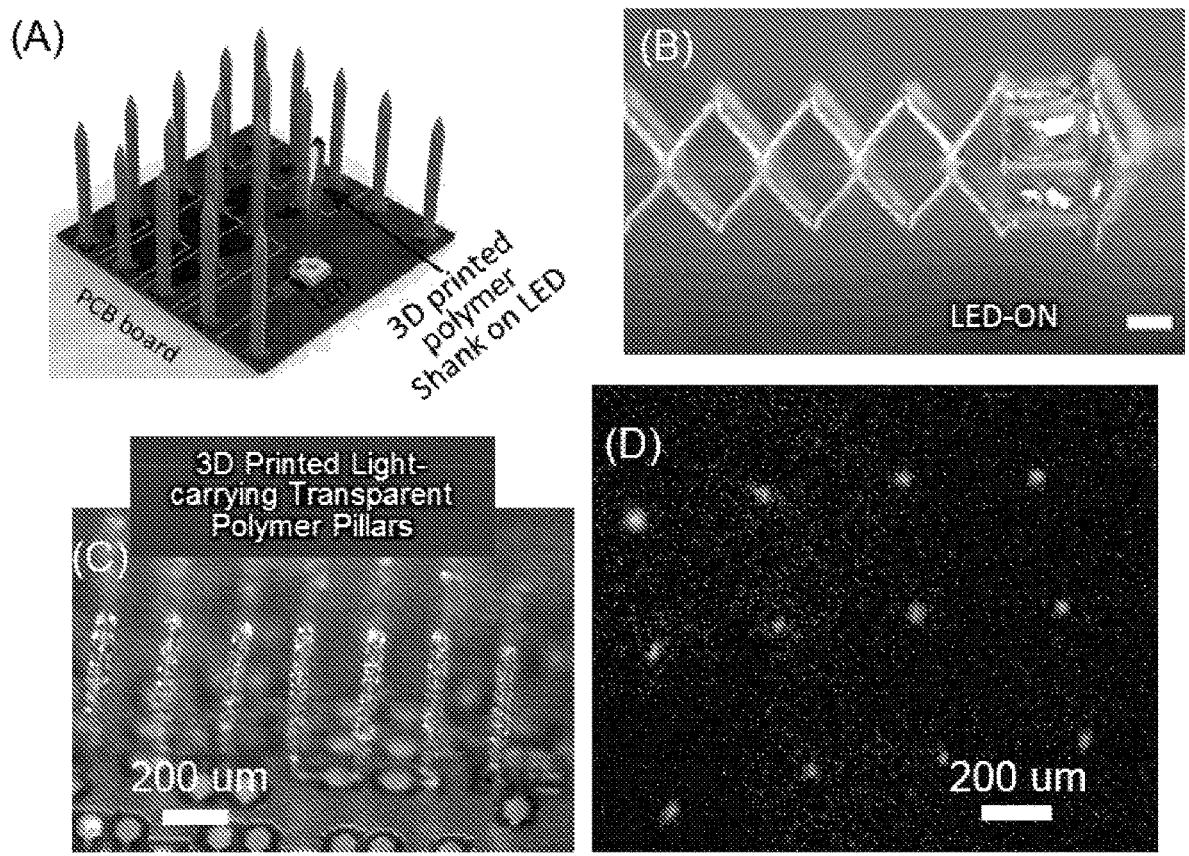
FIG. 7: Transparent polymer pillars for photo-stimulation of neurons: (A) Integrated polymer pillar with 3DP-MEA. The transparent polymer pillar transmits light from an LED on which the pillar is printed. (B) Interconnect printed on LED: a 3D printed metal connector was used to light the LED remotely. Bar=100 um. (C) Transparent polymer pillars of about 60 um diameter and 500 um tall printed on a Si microprocessor chip, (D) Insertion of polymer shank array into mouse brain (depth=650 um).

The waveguide-forming material can be directly printed over a diode or any other source of light. These pillars act as a waveguide for electromagnetic waves. The waveguide-forming material can be directly printed on a light-emitting diode (LED) surface (as shown in FIG. 7 (A)), that can be remotely turned on and off. The LED may produce infrared radiation, such as near infrared radiation. A schematic of a probe with a polymer optic fiber is shown in FIG. 7 (A). An LED can be affixed onto a PCB board on which the MEA is printed. The LED can be connected to the nearest pad using wire bonding or a 3D printed interconnect as shown in the photomicrograph of FIG. 7 (B). The optic fiber can be directly fabricated onto the LED by printing a transparent, light-conductive polymer.

The waveguide pillars and/or conductive shanks are formed by depositing over the surface of the substrate a plurality of layers of the waveguide-forming material or a conductive material. The nanoparticle solution forming the conducting shank or the solution from which the waveguide is formed can have a viscosity of greater than 1 cP and up to 1000 cP.

The nanoparticle solution or the solution from which the waveguide is fabricated can be dispensed using the Aerosol Jet machine in multiple layers. The process of printing of a conducting shank may involve deposition of one layer of the nanoparticle solution followed by the use of heat or other form of energy to remove the liquid medium. The solidified shank then forms a solid base to receive the next printed layer. This process is repeated to realize the high aspect ratio shanks shown in FIG. 1 without the need for any support material. The process of printing of a waveguide shank may involve deposition of one layers of the waveguide solution followed by the use of heat or UV light energy to remove the liquid medium. The solidified shank then forms a solid base to receive the next printed layer. This process is repeated to realize the high aspect ratio waveguide shanks shown in FIGS. 1D, 5, 7A, and 7C, without the need for any support material.

In one embodiment of the invention, the conducting shank can be made from conducting materials such as carbon black, or a conductive carbon allotrope, such as graphene, graphite, a fullerene, a carbon nanotube, or vitreous carbon. In such cases, the solution to be printed can be particles of these materials dispersed in a liquid medium.

Figure 8:
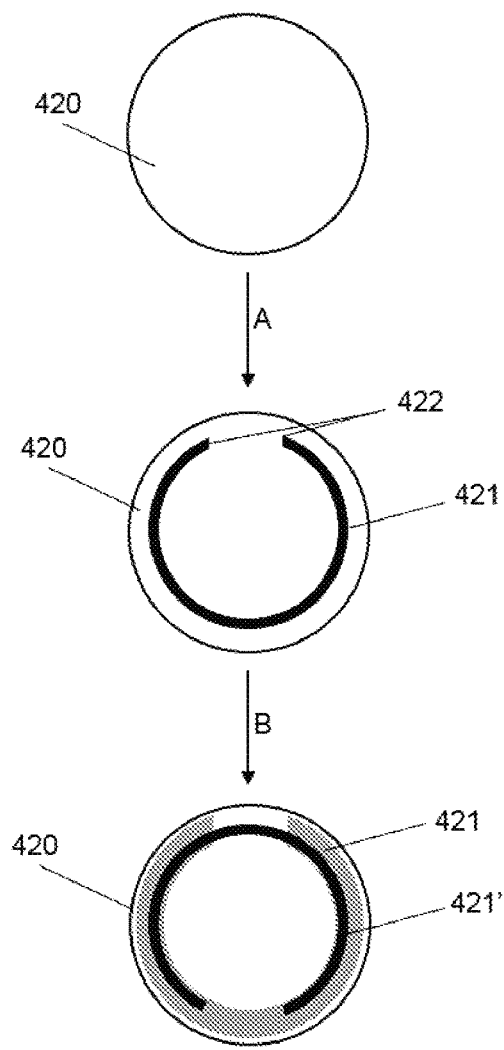
FIG. 8 depicts schematically the deposition of sequential, offset layers on a conductive stack or waveguide pillar as described herein.

FIG. 8 depicts a possible embodiment of sequential deposition of layers of material on a shank or pillar 420 as described herein. In a first step, "A", a layer of the material used to form the shank or pillar 420 is deposited as an open shape 421 having ends 422, defining a gap, e.g., a semi-circle. The open shape 421 may be a section of curved closed shape, such as a ring-shaped arc having a gap. The curved shape does not necessarily have to be circular. The gap may be less than 30%, such as less than 25%, 20%, 15%, or 10% of a perimeter of the shank. The open shape 421 is solidified by heat or any other source of energy. In a second step, "B", a second open shape 421' is deposited over the first open shape 421. The gaps of one or more adjacent layers may be offset with respect to each-other, as is shown. As is shown, open shape 421 spreads on the surface of the pillar, and therefore is depicted, for example, as a wider, closed shape in step B. The depicted steps A and B are exemplary and to form a pillar many such steps are necessary, the number of which determines the ultimate length of the pillar.

Figure 9:
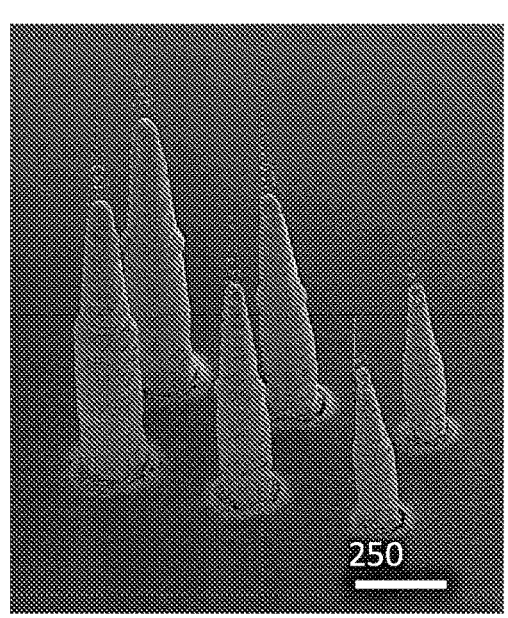
FIG. 9 is a photomicrograph showing pointed shank tip shapes.

The layers of the shank material may be deposited such that the shank is narrower at the tip to form shanks with a pointed shape, as shown in the photomicrograph of FIG. 9. For waveguide pillars, the deposition may not be as symmetrical as is shown in FIG. 9, but may be skewed, or the diameter of the deposited layers may increase forming a bulbous end, thereby forming a lens for directing light from the waveguide in a desired manner.

The printed shank material is then sintered or joined together by some means of energy such as laser, UV light, and thermal heat. Sintering is the process of compacting and forming a solid mass of material by heat or pressure without melting it to the point of liquefaction. Sintering happens naturally in mineral deposits or as a manufacturing process used with metals, ceramics, plastics, and other materials. In the context of nanoparticles, sintering is a heat treatment applied to a powder compact in order to impart strength and integrity. The temperature used for sintering is below the melting point of the major constituent of the powder metallurgy material. After compaction, neighboring powder particles are held together by cold welds, which give the compact sufficient "green strength" to be handled. At sintering temperature, diffusion processes cause necks to form and grow at these contact points. There are two requisites for this sintering mechanism to take place: first, water and other liquid medium or solvents, binders, rheology modifiers, anti-agglomeration coatings are removed by evaporation and burning, and second, surface oxides are reduced.

The metal nanoparticles of the conductive shank material can be sintered by raising the temperature to a temperature below the melting point of the metal nanoparticles at a rate of less than 5° C. per minute, such as 1° C. per minute. The nanoparticles may be sintered by heating to temperatures in the range of temperatures that varies with the material. For example, sintering for silver nanoparticles occur in a temperature range of from about 150° C. to 300° C. The liquid medium or solvents and/or binders in the shank material solution are partially or completely removed during the sintering operation.

The waveguide-forming material may be joined together or cured by a source of energy such as UV light or heat. The waveguide-forming material can be instantaneously cured and harden as it is formed during printing. During deposition, the substrate can be heated to cause complete or incomplete, e.g. "B-stage", crosslinking of thermoset polymer layers to rigidize the structure sufficiently to complete deposition. Likewise during deposition, the shanks can be exposed to UV light to partly or completely cure a UV-curable polymer composition.

Figure 10:
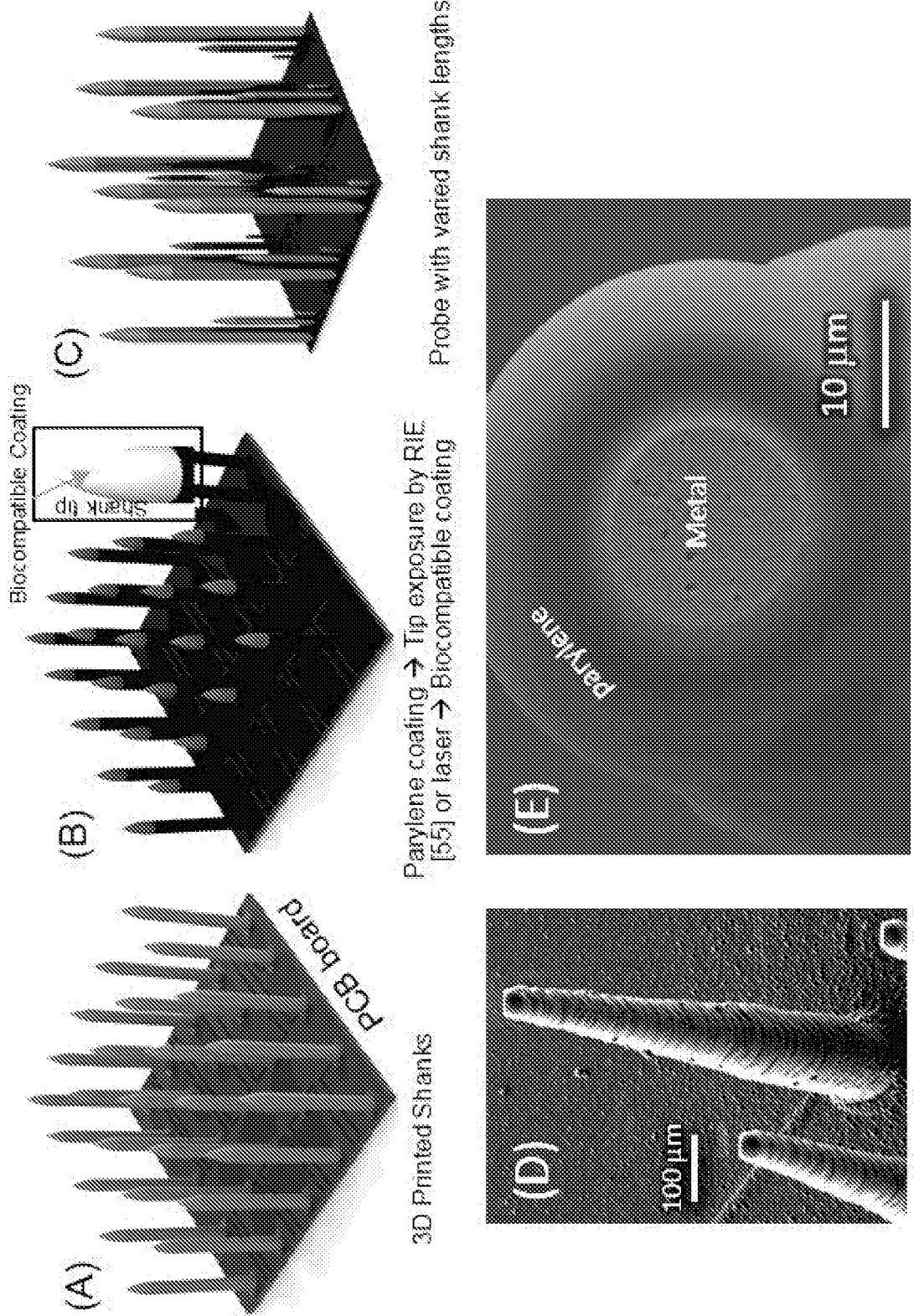
FIG. 10: 3D Printed Probe Production: (A) schematic of 3DP-MEA printed over a PCB substrate (B) schematic of parylene coating, tip exposure reactive ion etching, and biocompatible coating (e.g. PEDOT) at the tips using electrodeposition. (C) schematic of probe with different shank lengths. (D) 3DP-MEA with parylene coating (E) Exposed tip of the shank in (D) that can capture electrical signals from biological tissue such as neurons.

An insulator is deposited over a portion of the conductive-material shanks, leaving a conductive portion of the shank exposed, as shown in the photomicrograph of FIG. 10 (D). In one embodiment, the pillars are covered with an insulator except at the tip of the pillars (see, FIG. 10). The shanks are coated with an insulator through an appropriate deposition method (e.g. chemical vapor deposition or atomic layer deposition). The insulator can then be etched out using methods such as chemical etch or reactive ion etching or focused ion beam to leave a conductive portion of the shank exposed, such as the tip of the shank. In another embodiment, the insulator is deposited around the pillars by direct write and cured by an ultraviolet light. Non-limiting examples of suitable insulators include Parylene-C, Parylene-N, alumina, Teflon, and acrylic. An example of the removal of Parylene-C insulation from silver shanks using focused ion beam is shown in FIG. 10 (E) and FIG. 11 (A).

Another conductive material can be deposited over the exposed part of the conductive shank. The conductive material may be deposited only over the tip of the conductive shank, as shown schematically in FIG. 10 (B). The conductive material may be electroplated using standard techniques in the microelectronic industry. The conductive material may be deposited over the conductive shank by printing. The conductive material may be a biocompatible material. Non-limiting examples of conductive material include silver, gold, platinum, PEDOT (poly(2,3-dihydrothieno[3,4-b][1,4] dioxane-5,7-diyl) or poly(3,4-ethylenedioxythiophene)), PEDOT-PSS (a poly(3,4-ethylenedioxythiophene) polystyrene sulfonate mixture), PEDOT-TMA (poly(3,4-ethylenedioxythiophene)-tetramethacrylate copolymer), carbon black, or a conductive carbon allotrope, such as graphene, graphite, a fullerene, a carbon nanotube, or vitreous carbon. An example of electrodeposition of conductive PEDOT at the shank tip is shown in FIG. 11(B).

Each probe array may have a density of 1 to 20,000 shanks per $cm^2$, 500 to 10,000 shanks per $cm^2$, or 1,000-8,000 shanks per $cm^2$. For example, each array can have a density of greater than 100 shanks per $cm^2$, greater than 500 shanks per $cm^2$, or greater than 1,000 shanks per $cm^2$, such as 400, or 6,400 shanks per $cm^2$. The shank(s) can have different diameters along the length of the shank. Each shank is 1 µm to 1 mm in diameter. For example, each shank can have a diameter ranging from 10 µm to 200 µm, such as from 15 µm to 75 µm. The shanks may have a larger diameter closer to the substrate and a smaller diameter closer to the tip of the shank.

Each shank ranges from greater than 0 cm to 10 cm long, and in an array can be of the same length or a combination of lengths. For example, the probe may contain shanks that are 0, 0.5, 1.0, 1.5, 2, 3 and 4 mm in length all on the same probe. For example, each shank may have a length ranging from 10 µm to 10 cm, from 10 µm to 5 mm, from 10 µm to 1 mm, or from 50 µm to 1 cm. The shanks may be deposited perpendicular (normal), at a 90 degree angle to, substrate plane or at any other angle to the substrate between 1° to 90°. One or more of the shanks may be deposited normal to the substrate. One or more of the shanks may be deposited at an angle between 10° and 90° to the substrate. The matrix layout of the probe array can be any suitable shape, such as square, rectangular, triangular, hexagonal, or any other regular or irregular shape and/or pattern of shanks. In embodiments, the height (h) to diameter (d) ratios of the pillars of the probes can be from 0.1:1 to 100:1. The tips of the shank or pillars can be pointed or blunt. The shanks can be 3D printed straight, curved or any other shape needed for the end use.

In one embodiment, a method of making a conductive probe array is provided. The method comprises printing, using aerosol jet printing, a plurality of shanks on a substrate, e.g., in a density of from 1 to 20,000 shanks per $cm^2$. In one embodiment, metal particles are deposited to form a conductive shank, such as deposition of silver nanoparticles in a metallic ink comprising the nanoparticles and a liquid medium, and optionally a rheology modifier, such as ethylene glycol. In another embodiment, a transparent polymer is deposited to form a waveguide shank. The metallic ink or transparent polymer may be deposited in sequential layers of an open shape, such as a semi-circle, comprising a gap wherein the gaps of sequential layers are offset (not aligned), e.g., in semi-circles, as is shown in FIG. 8.

Where metal particles are deposited to form a conductive shank, the shanks are heated, e.g. by heating the substrate on which the shanks are deposited, to a temperature sufficient to evaporate a liquid medium in which the particles are deposited. This facilitates the production of a rigidized "green" structure that holds its form sufficiently during processing. After completion of the green structure, the shank is sintered at a suitable sintering temperature for the metallic particles, such as from about 150° C. to 300° C., e.g. 200° C., in the case of silver in a solution comprising ethylene glycol, such that the silver nanoparticles are sintered, and the ethylene glycol and solvents are evaporated and/or burned off. In one embodiment, the temperature is raised from the deposition temperature, e.g. the ambient temperature, at which the particles are deposited to the sintering temperature at a rate of less than 5° C. $minute^{-1}$, no more than 4° C. $minute^{-1}$, no more than 3° C. $minute^{-1}$, no more than 2° C. $minute^{-1}$, or no more than 1° C. $minute^{-1}$. The increase in temperature from the deposition temperature to the sintering temperature may be performed step-wise, for example in even steps of 1° C., 2° C., 3° C., 4° C., 5° C., 6° C., 7° C., 8° C., 9° C., or 10° C., or more, or less, or in uneven steps, or may be performed linearly, or according to any profile. In one aspect, the temperature is increased from the deposition temperature to the sintering temperature linearly at a rate of no more than 1° C. $minute^{-1}$. Where a transparent polymer is deposited to form a waveguide shank, the polymer is deposited, and is cured, e.g. by raising the temperature for a thermoset polymer, or by exposure to UV light for a UV curable polymer compositions.

Example 1-Synthesis of a 16 Channel 3DP-MEA Probe

A probe with 16-shanks, was 3D printed using an Aerosol Jet printer. The shank material is sintered silver nanoparticles.

Figure 11:
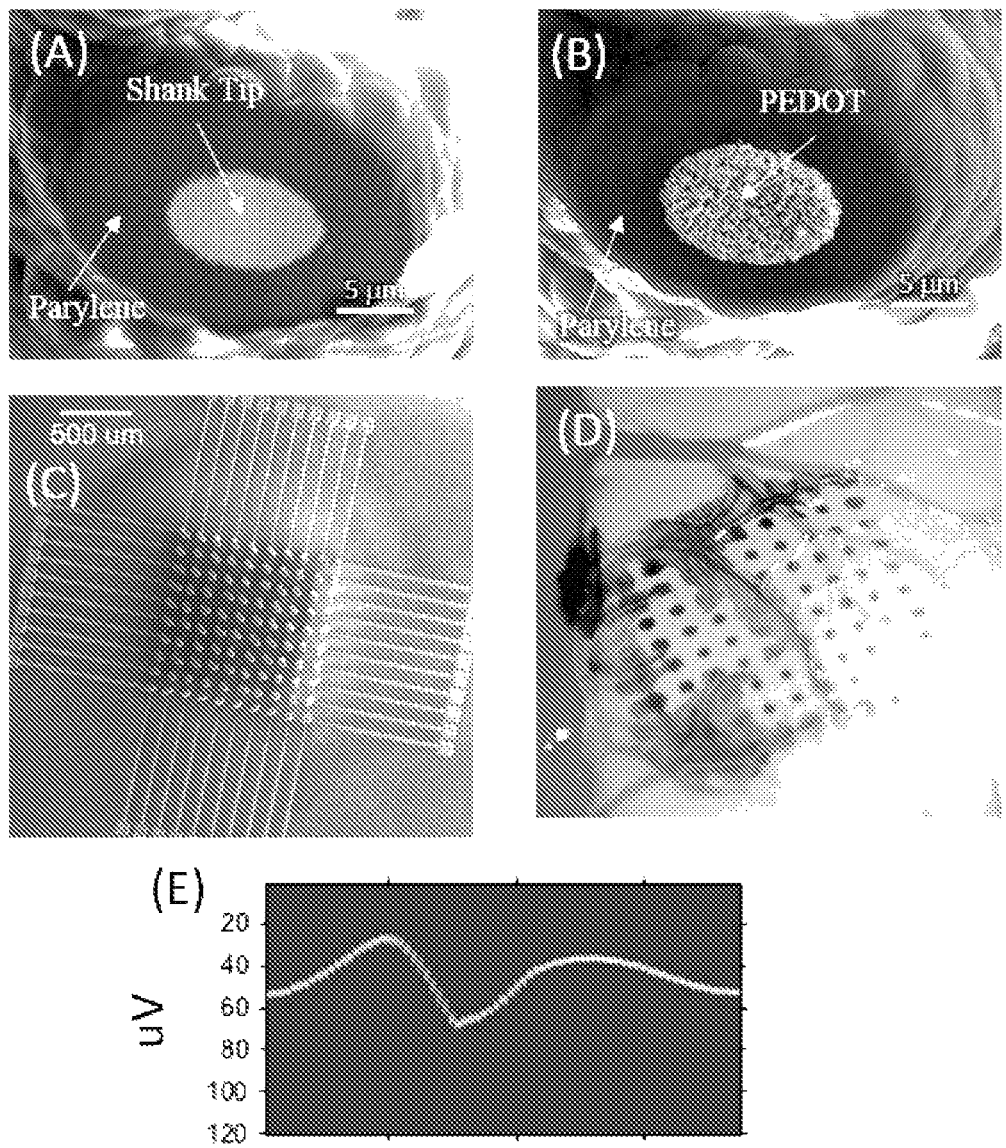
FIG. 11: Characterization, Penetration, and Recording. (A) Functionalization of the shank tips using focused ion beam to record neural signal, (B) Selective deposition of PEDOT, a conductive polymer at the tip of the shank to improve impedance, (C) Probe with 100-shank, 120-micron pitch, 20 um diameter 3D printed probe demonstrating 6400 shanks/cm$^2$. (D) Successful insertion of same probe using a stereotax (tracer dye left behind). (E) Recording of Signal: in vivo neural recording using a 16 channel 3DP-MEA probe from layer 5 in V1 of an anesthetized mouse.

The shank tips were coated with parylene as shown in FIG. 11 (A). The electrical impedance of an individual shank tip was of the order of 100 kΩ at 1 kHz frequency. PEDOT was selectively deposited at the tip of the shank as shown in FIG. 11 (B). The probe was successfully inserted into a mouse brain. The probe was used to record extracellular neural signals from the head-fixed mouse. In vivo neural recording was performed in the anesthetized mouse and is shown in FIG. 11 (E). The probe was used to make the recordings from isolated neurons about 600 um deep inside the brain at a time scale of about a millisecond.

Example 2-Synthesis of a 100 Channel 3DP-MEA Probe at a Density of 6400 Shanks/cm²

A probe with 100-shanks, each having 20 um diameter, and 120 um pitch was 3D printed using aerosol jet printing method. The recording density of the probe was 6400 shanks/cm2 and is shown in FIG. 11 (C). The probe was successfully inserted into an anesthetized mouse brain and dura as shown in FIG. 11 (D). Multiple insertions using a benchtop stereotax were carried out. The results demonstrated robustness of the probe with no indication of shank breakage. It was observed that there was minimal gross tissue damage surrounding the penetration holes.

Example 3-Synthesis of a 3DP-MEA with Long Shanks

Figure 12:
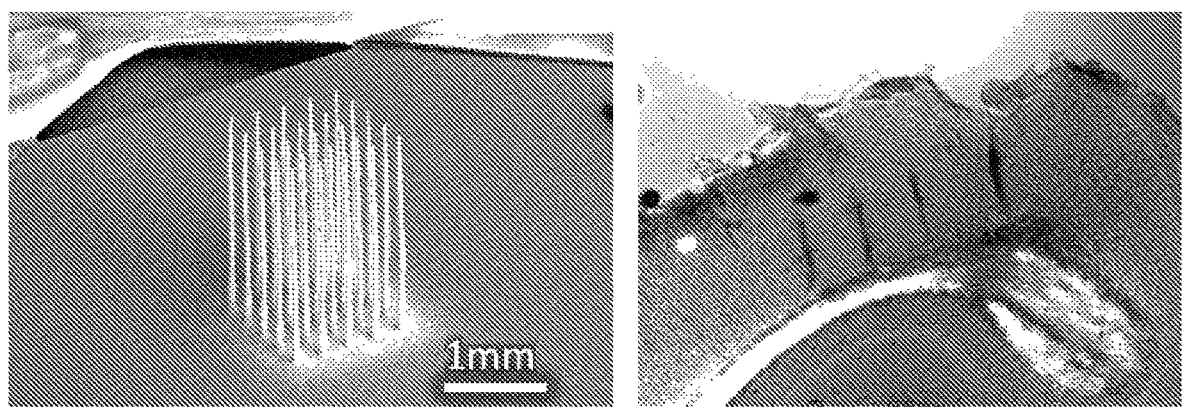
FIG. 12: Long Shanks (left) Electron micrograph of 2 mm long shanks with a 30:1 aspect ratio; with shank diameter 75 um at bottom and 15 um at top. AutoCAD program created the diameter variation for the shanks which are suitable for penetration. (right) Successful insertion test in an anesthetized mouse without breaking the shanks or gross damage to the brain (area V2, hippocampus).

A probe with long shanks that have a length, >2 mm, with shank diameter 75 um at bottom and 15 um at top was 3D printed as shown in FIG. 12. The long length was obtained by increasing the number of printed layers during the deposition process. AutoCAD program created the diameter variation for the shanks which are suitable for penetration. The aspect ratio of the 3D printed shanks is greater than 30:1.

The probe showed successful penetration through the mouse dura and brain to hippocampus region in an anesthetized mouse (FIG. 12, right, area V2, hippocampus). No breakage of the shanks or gross damage to the brain was observed.

Example 4-Printing of Multi-Layer PCB

Figure 13:
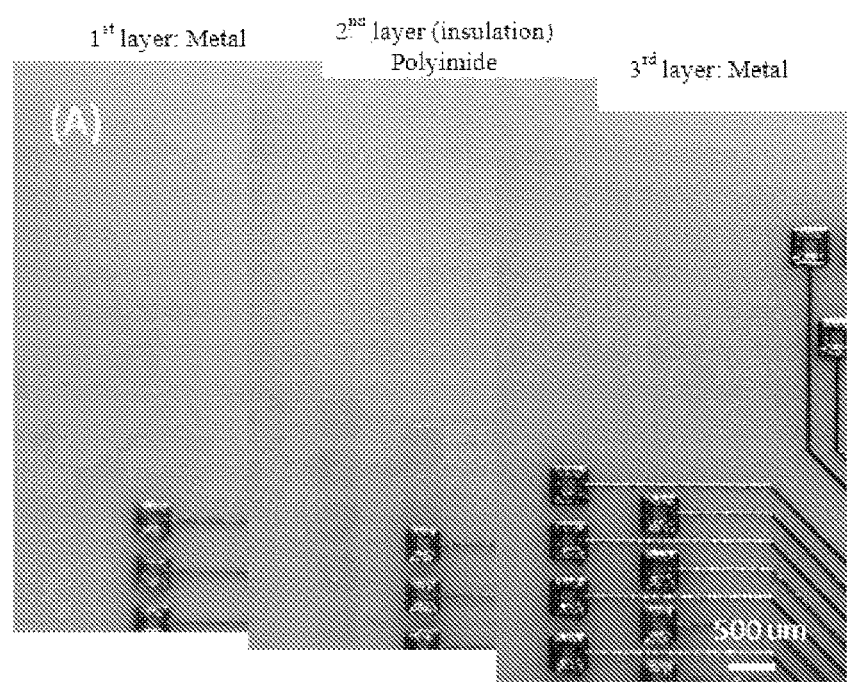
FIG. 13: (A, B) photomicrographs showing direct printing of multi-layer PCB board to connect the shanks to external pads.
Figure 13:
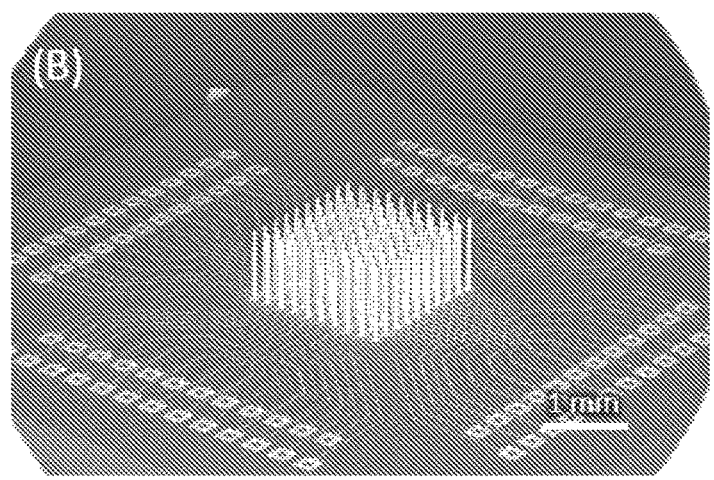

A multi-layer PCB was printed to connect the probe shanks to external pads. The electrical connectors were printed by AJ printing. A $1^{st}$ layer of metal was printed, followed by second insulation layer of polyimide, followed by a $3^{rd}$ layer of metal, as shown in FIG. 13 (A). The first and third metal layers in the PCB in FIG. 13(A) were isolated from each other by printing of polymer. This process created a multi-layer PCB board connecting individual shanks to an external lead as shown in FIG. 13(B). Note that in this example, the shank density is 2500 shanks/cm². Any number of additional layers is possible. With adequate multi-layer design and routing, it is are possible that to connect shanks at as high a density as 10,000 shanks/cm².

The PCB voltages route directly (through multiple Omentics 64 ch connectors) to the Intan RHD2000-64 ch digital head stages and 1024 ch recording controller.

Example 5-Synthesis of 3DP-MEA Probe with Both Metal and Polymer Shanks

An LED of about 200 um thickness is affixed onto a PCB board on which the 3DP-MEA is printed as shown in FIG. 1(D). The LED is connected to the nearest pad using either printing of connectors shown in FIG. 7(B) or a printed wire or a wire bond or any other connection process that powers the LED. The optic fiber was directly fabricated onto the LED by printing transparent, light-conductive polyimide. The polyimide was cured by a source of energy such as UV light or heat or microwave energy or photonic flash or a combination of one or more sources. The probe is shown in FIG. 1 (D).

Example 6-Synthesis of Probe with Polymer Shanks on Si Microprocessor Chip

Transparent polyimide shanks of about 60 um diameter and 500 um height were 3D printed on a Si microprocessor chip as shown in FIG. 7 (C). The polyimide pillars were rigid with a modulus in the range of 2.5 GPa. The polymer shank array was successfully inserted into mouse brain with no gross tissue damage, shown in FIG. 7 (D).

Figure 14:
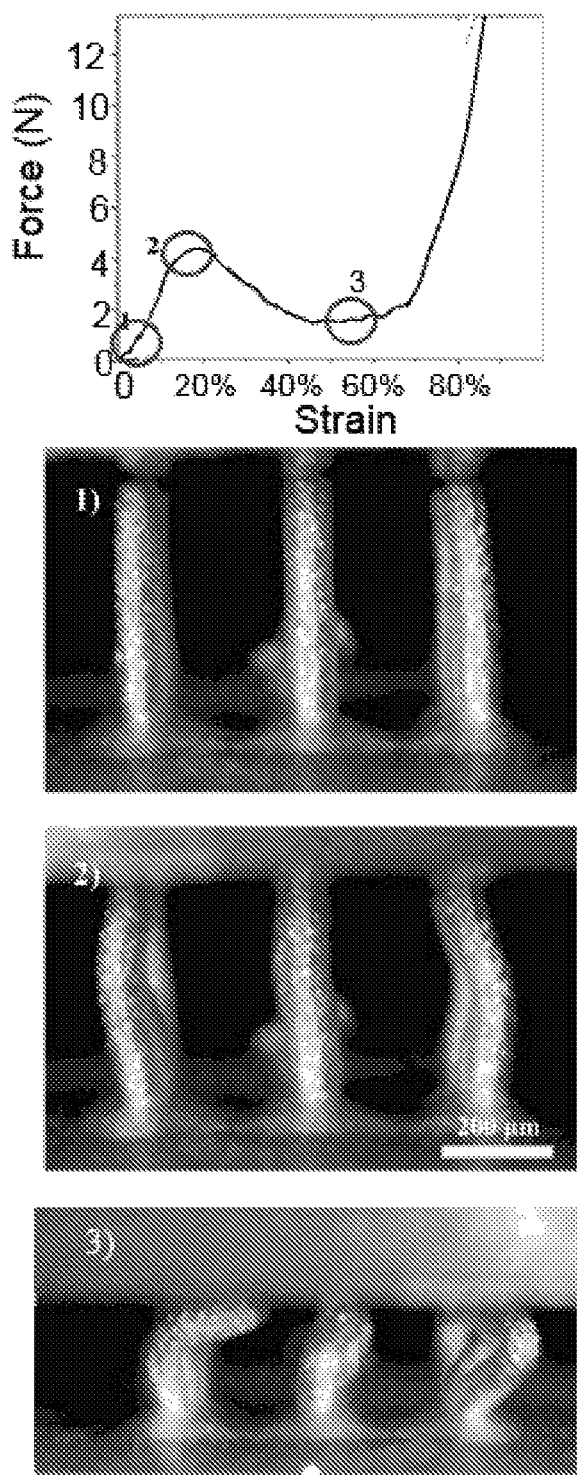
FIG. 14: graph and photomicrographs showing compression test of 3DP-MEA shanks. Shanks under various forces of compression (points 1, 2 and 3 of graph) do not break even under a displacement of 60% under a rigid platen.

Compression tests: 75 um silver shanks were placed under various points of compression as shown in FIG. 14. A rigid stainless steel platen was used to obtain the force-displacement relationship for the shanks. The shanks did not break after 60% displacement and a bending radius of <50 um as shown.

The following numbered clauses describe various aspects of the invention:

1. A method of preparing a high-density array of electrically-conductive, or optically-conductive shanks, comprising:
    depositing by aerosol jet printing, a plurality of shanks onto a surface of a substrate in a density of greater than 100 shanks per square centimeter of the surface of the substrate, each shank having a diameter ranging from 10 µm to 1 mm, and a length ranging from 10 µm to 10 cm, wherein the shanks are formed by depositing over the surface of the substrate a plurality of layers of a shank material solution comprising a conductive material dispersed in a liquid or a waveguide-forming material in a solvent, where each layer of the plurality of layers is deposited as an open shape having ends and a gap defined by the ends.

2. The method of clause 1, further comprising after deposition of every one to 50 layers, exposing the shanks to a heat or energy source, such as continuous heat, such as from 90° C. to 110° C., to remove the liquid or solvent, and/or to at least partly crosslink the waveguide-forming material.

3. The method of clause 1 or 2, wherein the shanks have an aspect ratio of diameter to length ranging from 1:1 to 1:1000.

4. The method of any one of clauses 1-3, wherein gaps of one or more adjacent layers are offset with respect to each-other.

5. The method of any one of clauses 1-4, wherein the open shape of the plurality of layers is a section of curved closed shape.

6. The method of any one of clauses 1-4, wherein the open shape is a semicircle.

7. The method of any one of clauses 1-6, wherein the layers are deposited in a solution having a viscosity of greater than 1 Cp.

8. The method of clause 7, wherein the layers are deposited in a solution having a viscosity ranging from 1 to 1000 Cp.

9. The method of any one of clauses 1-8, wherein the gap is less than 30%, 25%, 20%, 15%, or 10% of a perimeter of the shank.

10. The method of any one of clauses 1-9, wherein one or more of the shanks are deposited normal to the substrate.

11. The method of any one of clauses 1-9, wherein one or more of the shanks are deposited at an angle between 10 and 90 degrees relative to the plane of the substrate.

12. The method of any one of clauses 1-11, wherein layers are deposited to form a tapered shank.

13. The method of any one of clauses 1-12, wherein one or more of the shanks is prepared by depositing a waveguide-forming material on the substrate.

14. The method of clause 13, wherein the waveguide-forming material is a transparent polymer, optionally having >1% transmittance over the length of the shank.

15. The method of clause 14, wherein the waveguide is formed from a photopolymer or a thermosetting polymer.

16. The method of clause 13, further comprising curing the waveguide-forming material.

17. The method of any one of clauses 13-16, wherein the waveguide-forming material is deposited over a light-emitting diode (LED), wherein the LED optionally produces infrared radiation, such as near infrared radiation.

18. The method of any one of clauses 1-17, wherein the substrate is a circuit board or an integrated circuit.

19. The method of clause 18, wherein the substrate is a printed circuit board.

20. The method of clause 19, wherein traces on the printed circuit board are deposited by aerosol jet printing.

21. The method of any one of clauses 1-10, wherein an electrically-conductive material is deposited to form the conductive shanks.

22. The method of clause 21, wherein the electrically-conductive material comprises metal nanoparticles.

23. The method of clause 21, wherein the metal particles are deposited with a binder.

24. The method of clause 21, further comprising sintering the metal nanoparticles in the conductive shanks.

25. The method of clause 24, wherein the metal nanoparticles are sintered by raising the temperature to a temperature below the melting point of the metal nanoparticles at a rate of less than 5° C. per minute, or 1° C. or less per minute.

26. The method of clause 21, further comprising depositing a conductive material over the conductive shank.

27. The method of clause 26, wherein the conductive material comprises silver, gold, platinum, PEDOT (poly(2,3-dihydrothieno[3,4-b][1,4]dioxane-5,7-diyl) or poly(3,4-ethylenedioxythiophene)), PEDOT-PSS (a poly(3,4-ethylenedioxythiophene) polystyrene sulfonate mixture), PEDOT-TMA (poly(3,4-ethylenedioxythiophene)-tetramethacrylate copolymer), carbon black, or a conductive carbon allotrope, such as graphene, graphite, a fullerene, a carbon nanotube, or vitreous carbon.

28. The method of any one of clauses 1-27, further comprising depositing an insulator over a portion of at least one of the shanks, leaving a portion of the shank exposed.

29. The method of clause 28, wherein the tip of the at least one shank is not covered with an insulator.

30. A microprobe array comprising a plurality of conductive shanks and/or waveguide shanks over an LED on a surface of a substrate, each shank having a thickness ranging from 10μ to 1 mm, and ranging from 50μ to 1 cm in length, and disposed on the surface in a density of at least 100 shanks per cm².

31. The array of clause 30, comprising a plurality of waveguide shanks over an LED.

32. The array of clause 30, comprising conductive shanks comprising sintered metal nanoparticles.

33. The array of clause 32, wherein the metal comprises silver, gold, platinum, or copper.

34. The array of any one of clauses 30-33, wherein the substrate is an integrated circuit or a circuit board and the conductive shanks or LEDs are electrically-connected to interconnects of the integrated circuit or traces of a circuit board.

35. The array of any one of clauses 30-34, wherein at least two of the shanks are independently addressable.

36. The array of any one of clauses 30-35, wherein the substrate is a printed circuit board.

37. The array of any one of clauses 30-36, further comprising both conductive shanks and one or more LEDs and an optical waveguide shank over the LED, wherein the LED optionally produces infrared radiation, such as near infrared radiation.

38. The array of any one of clauses 30-37, wherein the waveguide shank comprises a transparent polymer, optionally having >1% transmittance over the length of the shank.

39. The array of any one of clauses 30-38, wherein one or more of the conductive shanks comprise a layer of conductive material over the conductive shank.

40. The array of clause 39, wherein the conductive material comprises silver, gold, platinum, PEDOT (poly(2,3-dihydrothieno[3,4-b][1,4]dioxane-5,7-diyl) or poly(3,4-ethylenedioxythiophene)), PEDOT-PSS (a poly(3,4-ethylenedioxythiophene) polystyrene sulfonate mixture), PEDOT-TMA (poly(3,4-ethylenedioxythiophene)-tetramethacrylate copolymer), carbon black, or a conductive carbon allotrope, such as graphene, graphite, a fullerene, a carbon nanotube, or vitreous carbon.

41. The array of any one of clauses 30-40, further comprising depositing an insulator over at least a portion of at least one of the conductive shanks.

42. The array of clause 41, wherein at least a portion of the at least one conductive shank is not covered with an insulator.

43. The array of any one of clauses 30-42, the shanks have a thickness ranging from 10μ to 1 mm, a length ranging from 50μ to 10 cm, and a density on the surface of from 50 to 500 shanks per cm², from 100 to 400 shanks per cm², or at least 100 shanks per cm², or at least 1,000 shanks per cm².

44. A bioprobe system comprising an array of any one of clauses 30-42, a plurality of leads attached independently to a plurality of conductive shanks of the array, and module configured to send to electrical signals to a shank or LED and/or receive an electrical stimulator from the shank, the module comprising a signal amplifier, a filter, and one or more processors and/or controllers configured or adapted to communicate electrical signals to and from the shanks or LEDs of the array.

45. The bioprobe system of clause 44, wherein the array comprises one or more LEDs, and one or more optical waveguide shanks over each of the LEDs.

46. The bioprobe system of clause 44, wherein the array comprises one or more conductive shanks.

47. A method of interfacing with tissue in a patient, comprising, implanting the array according to any one of clauses 30-42 in tissue of the patient so that a conductive surface of one or more conductive shanks of the array is positioned to administer an electrical signal to, or receive an electrical signal from tissue of the patient, and/or a waveguide shank is positioned to administer an optical signal to the tissue of the patient, and administering an electrical signal to the tissue of the patient, receiving an electrical signal from the tissue of the patient, and/or administering an optical signal to the tissue of the patient.

48. The method of clause 47, comprising interfacing with one or more neurons in a patient by implanting the array in tissue of the patient so that a conductive surface of one or more conductive shanks of the array is positioned to administer an electrical signal or receive an electrical signal from one or more neurons of the patient, and/or more waveguide shanks is positioned to administer an optical signal to one or more neurons of the patient, and administering an electrical signal to the one or more neurons of the patient, receiving an electrical signal from the one or more neurons of the patient, and/or administering an optical signal to the one or more neurons of the patient.

49. The method of clause 47, wherein the tissue is central nervous system tissue, such as spinal cord tissue or brain tissue.

50. The method of clause 47, wherein the tissue comprises peripheral nerve tissue.

51. Use of an array according to any one of clauses 30-42, for stimulating a neuron, and/or for receiving an electrical signal from tissue, such as a neuron.

52. The array of any one of clauses 30-42, for use in stimulating a neuron, and/or for receiving an electrical signal from tissue, such as a neuron.

Having described this invention, it will be understood to those of ordinary skill in the art that the same can be performed within a wide and equivalent range of conditions, formulations and other parameters without affecting the scope of the invention or any embodiment thereof.

What is claimed is:

1. A method of preparing a high-density array of electrically-conductive, or optically-conductive shanks, comprising:
depositing by aerosol jet printing, a plurality of shanks onto a surface of a substrate in a density of greater than 100 shanks per square centimeter of the surface of the substrate, each shank having a diameter ranging from 10 μm to 1 mm, and a length ranging from 10 μm to 10 cm, wherein the shanks are formed by depositing over the surface of the substrate a plurality of layers of a shank material solution comprising a conductive material dispersed in a liquid or a waveguide-forming material in a solvent, where each layer of the plurality of layers is deposited as an open shape having ends and a gap defined by the ends.

2. The method of claim 1, further comprising after deposition of every one to 50 layers, exposing the shanks to a heat or energy source to remove the liquid or solvent, and/or to at least partly crosslink the waveguide-forming material.

3. The method of claim 2, wherein the shanks are exposed to continuous heat.

4. The method of claim 3, wherein the continuous heat is from 90° C. to 110° C.

5. The method of claim 1, wherein the shanks have an aspect ratio of diameter to length ranging from 1:1 to 1:1000.

6. The method of claim 1, wherein gaps of one or more adjacent layers are offset with respect to each other.

7. The method of claim 1, wherein layers are deposited to form a tapered shank.

8. The method of claim 1, wherein one or more of the shanks is prepared by depositing a waveguide-forming material over a light-emitting diode (LED) on the substrate.

9. The method of claim 1, wherein the substrate is a circuit board or an integrated circuit, wherein traces on the printed circuit board are deposited by aerosol jet printing.

10. The method of claim 1, wherein an electrically-conductive material is deposited to form the conductive shanks.

11. The method of claim 10, wherein the electrically-conductive material comprises metal nanoparticles, and further comprising sintering the metal nanoparticles.

12. The method of claim 11, wherein the metal nanoparticles are sintered by raising the temperature to a temperature below the melting point of the metal nanoparticles at a rate of less than 5° C. per minute.

13. The method of claim 10, further comprising depositing a conductive material over the conductive shank.

14. The method of claim 13, wherein the conductive material comprises silver, gold, platinum, PEDOT (poly(3,4-ethylenedioxythiophene)), PEDOT-PSS (a poly(3,4-ethylenedioxythiophene) polystyrene sulfonate mixture), PEDOT-TMA (a poly(3,4-ethylenedioxythiophene)-tetramethacrylate copolymer), carbon black, or a conductive carbon allotrope.

15. The method of claim 14, wherein the conductive carbon allotrope comprises graphene, graphite, a fullerene, a carbon nanotube, or vitreous carbon.

16. The method of claim 10, further comprising depositing an insulator over a portion of at least one of the shanks, leaving a portion of the shank, exposed.

17. The method of claim 16, wherein the tip of the shank is exposed.

* * * * *